(12) United States Patent
Luo et al.

(10) Patent No.: US 12,076,367 B2
(45) Date of Patent: Sep. 3, 2024

(54) FUSION PROTEIN BETWEEN SHORT FORM ROD-DERIVED CONE VIABILITY FACTOR AND A HYDROPHILIC PEPTIDE

(71) Applicant: Pharma Cinq, LLC, Rockville, MD (US)

(72) Inventors: Tianci Luo, Fulton, MD (US); Jun Zhang, Ellicott City, MD (US)

(73) Assignee: Pharma Cinq, LLC, Rockville, MD (US)

( * ) Notice: Subject to any disclaimer, the term of this patent is extended or adjusted under 35 U.S.C. 154(b) by 0 days.

(21) Appl. No.: 17/172,202

(22) Filed: Feb. 10, 2021

(65) Prior Publication Data

US 2021/0162005 A1    Jun. 3, 2021

Related U.S. Application Data

(62) Division of application No. 16/301,764, filed as application No. PCT/US2017/056030 on Oct. 11, 2017, now Pat. No. 10,946,063.

(60) Provisional application No. 62/406,552, filed on Oct. 11, 2016.

(51) Int. Cl.
| | |
|---|---|
| *A61K 38/17* | (2006.01) |
| *A61K 47/42* | (2017.01) |
| *A61K 47/64* | (2017.01) |
| *A61P 25/14* | (2006.01) |
| *C07K 14/47* | (2006.01) |
| *C07K 14/76* | (2006.01) |
| *C12N 9/02* | (2006.01) |
| *C12N 15/11* | (2006.01) |
| *C12N 15/113* | (2010.01) |
| *C12N 15/85* | (2006.01) |
| *C12N 15/86* | (2006.01) |

(52) U.S. Cl.
CPC .......... *A61K 38/1709* (2013.01); *A61K 47/42* (2013.01); *A61K 47/643* (2017.08); *A61P 25/14* (2018.01); *C07K 14/47* (2013.01); *C07K 14/76* (2013.01); *C12N 9/0036* (2013.01); *C12N 15/111* (2013.01); *C12N 15/113* (2013.01); *C12N 15/85* (2013.01); *C12N 15/86* (2013.01); *C12Y 108/01008* (2013.01); *C07K 2319/02* (2013.01); *C07K 2319/31* (2013.01); *C12N 2750/14143* (2013.01); *C12N 2800/22* (2013.01)

(58) Field of Classification Search
None
See application file for complete search history.

(56) References Cited

U.S. PATENT DOCUMENTS

| | | | |
|---|---|---|---|
| 8,071,745 B2 | 12/2011 | Leveillard | |
| 8,114,849 B2 | 2/2012 | Leveillard | |
| 8,394,756 B2 | 3/2013 | Leveillard | |
| 8,518,695 B2 | 8/2013 | Leveillard | |
| 9,265,813 B2 | 2/2016 | Luo | |
| 10,040,835 B2 | 8/2018 | Luo | |
| 10,105,452 B2 | 10/2018 | Hamel et al. | |
| 2003/0018984 A1 | 1/2003 | Coleman et al. | |
| 2004/0063635 A1 | 4/2004 | Yu et al. | |
| 2005/0054570 A1 | 3/2005 | Rosen et al. | |
| 2007/0141557 A1 | 6/2007 | Raab et al. | |
| 2009/0215679 A1 | 8/2009 | Leveillard et al. | |
| 2011/0034546 A1 | 2/2011 | O'Riordan et al. | |
| 2012/0088819 A1 | 4/2012 | Inoue et al. | |
| 2012/0108657 A1 | 5/2012 | Leveillard | |
| 2012/0245093 A1 | 9/2012 | Leveillard | |
| 2014/0050713 A1 | 2/2014 | Appaiah et al. | |
| 2014/0066378 A1 | 3/2014 | Dixit et al. | |
| 2014/0328821 A1 | 11/2014 | Luo | |
| 2016/0108099 A1 | 4/2016 | Luo | |

(Continued)

FOREIGN PATENT DOCUMENTS

| | | |
|---|---|---|
| JP | H07241196 A | 9/1995 |
| JP | 2010-529958 A | 9/2010 |
| JP | 2014-516358 A | 7/2014 |

(Continued)

OTHER PUBLICATIONS

National Eye Institute entry (retrieved from https://www.nei.nih.gov/learn-about-eye-health/eye-conditions-and-diseases/age-related-macular-degeneration#:~:text=Dry%20AMD%20happens%20in%203,to%20protect%20your%20other%20eye. on Mar. 17, 2022, 7 pages) (Year: 2022).*

(Continued)

*Primary Examiner* — Ronald T Niebauer
(74) *Attorney, Agent, or Firm* — MEDLER FERRO WOODHOUSE & MILLS PLLC (57) ABSTRACT

A fusion protein is described, comprising a first N-terminal signal peptide sequence, a second peptide sequence C-terminal to the signal peptide sequence, and a third peptide sequence C-terminal to the second peptide sequence; wherein one of the second peptide sequence and the third peptide sequence is an RdCVF-short peptide sequence and the other is a hydrophilic peptide sequence. After translation the signal peptide is cleaved, leaving a fusion protein comprising the second peptide sequence and the third peptide sequence minus the signal peptide. Also described are nucleic acids and expression vectors encoding the fusion protein, cells comprising the nucleic acid or expression vector, as well as methods of treatment and uses of the fusion protein, nucleic acid, and expression vector. The fusion protein can be produced in vitro by culturing the cells of this invention under conditions allowing for expression and secretion of the encoded fusion protein, and isolating the fusion protein from the cell culture.

10 Claims, 2 Drawing Sheets

Specification includes a Sequence Listing.

(56) References Cited

U.S. PATENT DOCUMENTS

2018/0369415 A1    12/2018    Bennicelli et al.

FOREIGN PATENT DOCUMENTS

| JP | 2015-501156 A | 1/2015 |
|---|---|---|
| RU | 2384586 C2 | 3/2010 |
| WO | 2002081513 A2 | 10/2002 |
| WO | 2008148860 A1 | 12/2008 |
| WO | 2009146183 A1 | 12/2009 |
| WO | 2010029130 A1 | 3/2010 |
| WO | 2013063383 A2 | 5/2013 |

OTHER PUBLICATIONS

American Parkinson Disease Association entry (retrieved from https://www.apdaparkinson.org/what-is-parkinsons/symptoms/eye-vision-issues/#:~:text=People on Mar. 16, 2022, 7 pages) (Year: 2022).*
NIH entry (retrieved from https://www.nidcd.nih.gov/health/smell-disorders on Mar. 16, 2022, 7 pages) (Year: 2022).*
Genbank Accession No. NP_612463 "nucleoredoxin-like protein 1 [Homo sapiens]." Feb. 26, 2014.
Genbank Accession No. XM_008508685 "Predicted: Equus przewalskii nucleoredoxin-like 1 (NXNL1), mRNA" Jul. 14, 2014.
Ait-Ali et al., "Rod-derived cone viability factor promotes cone survival by stimulating aerobic glycolysis", Cell (May 7, 2015) 161: 817-832.
Andrews et al., "Sequences beyond the cleavage site influence signal peptide function", J. Biol. Chem. (Oct. 25, 1988) 263(30): 15791-15798.
Choo et al., "Flanking signal and mature peptide residues influence signal peptide cleavage", BMC Bioinformatics (Dec. 12, 2008) 9(Suppl 12):S15, 11 pages. <doi.10.1186/1147 1-2105-9-S12-S15>.
Neto et al., "Skeletal muscle signal peptide optimization for enhancing propeptide or cytokine secretion", J. Theor. Biol. author manuscript, 15 pages, published in final edited form as: J. Theor. Biol. (Nov. 21, 2016) 409: 11-17. <doi:10:1016/j.jtbi.2016.08.036>.
Leveillard et al., "Identification and characterization of rod-derived cone viability factor", Nature Genetics (Jul. 2004) 36(7): 755-759.
Yang et al., "Functional cone rescue by RdCVF protein in a dominant model of retinitis pigmentosa", Molecular Therapy (2009) 17(5): 787-795.
Amado, "Gene therapy in the retina: exploring neurotrophic treatment and AAV readministration in retinal disease", PhD dissertation (2010), University of Pennsylvania, 131 pages.
Genbank Accession No. NM_138454 "Homo sapiens nucleoredoxin-like 1 (NXNL1), mRNA." Mar. 15, 2015.
Angov, "Codon usage: nature's roadmap to expression and folding of proteins", Biotechnol. J. (2011) 6: 650-659 <DOI 10.1002/biot.201000332>.
Byrne et al., "AAV-mediated delivery of rod-derived cone viability factor in a mouse model of retinal degeneration", Annual Meeting of the Association for Research in Vision and Ophthalmology (May 2, 2011) Presentation Abstract, Session 228, Program No. 1395.
Chalmel et al., "Rod-derived cone viability factor-2 is a novel bifunctional thioredoxi-like protein with therapeutic potential", BMC Molecular Biology (Aug. 31, 2007) 8:74, 12 pages. <doi:10.1186/1471-2199-8-74>.
Cronin et al., "The disruption of the rod-derived cone viability gene leads to photoreceptor dysfunction and susceptibility to oxidative stress", Author manuscript,24 pages, published in final edited form as: Cell Death Differ. (Jul. 2010) 17(7): 1199-1210. <doi:10.1038/cdd.2010.2>.
Fath et al., "Multiparameter RNA and codon optimization: a standardized tool to assess and enhance autologous mammalian gene expression", pLoS ONE (Mar. 2011) 6(3): e17596, 14 pages.
Jaillard et al., "Impaired vision and olfaction in mice lacking RdCVF2", ARVO Annual Meeting Abstract: Investigative Ophthalmology & Visual Science (Apr. 2009) 50:491.
Leveillard et al., "Rod-derived cone viability factor for treating blinding diseases: from clinic to redox signaling", Author manuscript, 10 pages, published in final edited form as: Sci. Transl. Med. (Apr. 2010) 2(26): 26ps16. <doi:10:1126/scitranslmed.3000866>.
McClements et al., "Gene therapy for retinal disease", Translational Research (Apr. 2013) 161(4): 241-254.
Mohand-Said et al., "Rod-cone interactions: developmental and clinical significance", Progress in Retinal and Eye Research (2001) 20(4): 451-467.
Plotkin et al., "Synonymous but not the same: the causes and consequences of codon bias", Author manuscript, 25 pages, published in final edited form as: Nat. Rev. Genet. (Jan. 2011) 12(1): 32-42. <doi:10:1038/nrg2899>.
Rocha, "Codon usage bias from tRNA's point of view: redundancy, specialization, and efficient decoding for translation optimization", Genome Research (2004) 14:2279-2286.
Sahel et al., "Rod-cone interdependence: implications for therapy of photoreceptor cell diseases", in Progress in Brain Research, Kolb et al. eds. (Elsevier 2001) vol. 131, ch. 47, pp. 649-661.
Wang et al., "Thioredoxin-like 6 protects retinal cell line from photooxidative damage by upregulating NF-[kappa]B activity", Free Radical Biology & Medicine (2008) 45: 336-344.
Wang et al., "Preventative immunization of optimized human [alpha]-synuclein DNA vaccine protects acute mouse with MPTP-induced parkinson's disease", Acta Academiae Medicinae Militaris Tertiae (Sep. 2009) 31(18): 1761-1765.
Fridlich et al., "The thioredoxin-like protein rod-derived cone viability factor (RdCVFL) interacts with TAU and inhibits its phosphorylation in the retina", Molecular & Cellular Proteomics (2009) 8(6): 1206-1218.
Byrne et al., "Viral-mediated RdCVF ad RdCVFL expression protects cone and rod photoreceptors in retinal degeneration", J. Clin. Invest. (Jan. 2015) 125(1): 105-116.
Léveillard et al., "Is Retinal Metabolic Dysfunction at the Center of the Pathogenesis of Age-related Macular Degeneration?", Int J Mol Sci. Feb. 11, 2019;20(3):762. doi: 10.3390/ijms20030762.PMID: 30754662.
Reichman et al., "The homeobox gene CHX10/VSX2 regulates RdCVF promoter activity in the inner retina", Hum Mol Genet. Jan. 15, 2010;19(2):250-61. doi: 10.1093/hmg/ddp484. Epub Oct. 20, 2009.PMID: 19843539.
Léveillard et al., "Cell Signaling with Extracellular Thioredoxin and Thioredoxin-Like Proteins: Insight into Their Mechanisms of Action", Oxid Med Cell Longev. 2017;2017:8475125. doi: 10.1155/2017/8475125. Epub Sep. 12, 2017. PMID: 29138681.
Narayan et al., "A review of the mechanisms of cone degeneration in retinitis pigmentosa", J.Acta Ophthalmol. Dec. 2016;94(8):748-754. doi: 10.1111/aos.13141. Epub Jun. 27, 2016.PMID: 27350263.
Chalmel et al., "Rod-derived Cone Viability Factor-2 is a novel bifunctional-thioredoxin-like protein with therapeutic potential", BMC Mol Biol. Aug. 31, 2007;8:74. doi: 10.1186/1471-2199-8-74. PMID: 17764561.
Camacho et al., "A Mathematical Analysis of Aerobic Glycolysis Triggered by Glucose Uptake in Cones", Sci Rep. Mar. 11, 2019;9(1):4162. doi: 10.1038/s41598-019-39901-z.PMID: 30858444.
Cronin et al., "The disruption of the rod-derived cone viability gene leads to photoreceptor dysfunction and susceptibility to oxidative stress", Cell Death Differ. Jul. 2010;17(7):1199-210. doi: 10.1038/cdd.2010.2. Epub Feb. 5, 2010.PMID: 20139892.
Elachouri et al., "Thioredoxin rod-derived cone viability factor protects against photooxidative retinal damage", Free Radic Biol Med. Apr. 2015;81:22-9. doi: 10.1016/j.freeradbiomed.2015.01.003. Epub Jan. 14, 2015.PMID: 25596499.
Dalkara et al., "Gene therapy for inherited retinal degenerations", C R Biol. Mar. 2014;337(3):185-92. doi: 10.1016/j.crvi.2014.01.002. Epub Mar. 11, 2014.PMID: 24702845.
Léveillard et al., "Therapeutic strategy for handling inherited retinal degenerations in a gene-independent manner using rod-derived cone viability factors", C R Biol. Mar. 2014;337(3):207-13. doi: 10.1016/j.crvi.2013.12.002. Epub Feb. 20, 2014.PMID: 24702847.

(56) References Cited

OTHER PUBLICATIONS

Krol et al., "Rods Feed Cones to Keep them Alive", Cell. May 7, 2015;161(4):706-8. doi: 10.1016/j.cell.2015.04.031. PMID: 25957678.
Sahel et al., "Functional rescue of cone photoreceptors in retinitis pigmentosa",Graefes Arch Clin Exp Ophthalmol. Jul. 2013;251(7):1669-77. doi: 10.1007/s00417-013-2314-7.PMID: 23575948.
Hayashi et al., "Nucleoredoxin negatively regulates Toll-like receptor 4 signaling via recruitment of flightless-I to myeloid differentiation primary response gene (88)", J Biol Chem. Jun. 11, 2010;285(24):18586-93. doi: 10.1074/jbc.M110.106468. Epub Apr. 16, 2010.PMID: 20400501.
Clérin et al., "Metabolic and Redox Signaling of the Nucleoredoxin-Like-1 Gene for the Treatment of Genetic Retinal Diseases", Int J Mol Sci. Feb. 27, 2020;21(5):1625. doi: 10.3390/ijms21051625. PMID: 32120883.
Léveillard et al., "Rod-derived cone viability factor for treating blinding diseases: from clinic to redox signaling", Sci Transl Med. Apr. 7, 2010;2(26):26ps16. doi: 10.1126/scitranslmed.3000866. PMID: 20375363.
Mei et al., "The Thioredoxin Encoded by the Rod-Derived Cone Viability Factor Gene Protects Cone Photoreceptors Against Oxidative Stress", Antioxid Redox Signal. Jun. 1, 2016;24(16):909-23. doi: 10.1089/ars.2015.6509. Epub May 12, 2016.PMID: 27025156.
Sahel et al., "Retinopathies pigmentaires : de la therapie cellulaire a la signalisation intercellulaire [Neuroprotection of photoreceptor cells in rod-cone dystrophies: from cell therapy to cell signalling]", C R Biol. Feb. 2005;328(2):163-8. doi: 10.1016/j.crvi.2004.12.007. PMID: 15771002.
Wang et al., "Thioredoxin-like 6 protects retinal cell line from photooxidative damage by upregulating NF-kappaB activity", Free Radic Biol Med. Aug. 1, 2008;45(3):336-44. doi: 10.1016/j.freeradbiomed.2008.04.028. Epub Apr. 26, 2008.PMID: 18474255.
Jaillard et al., "Nxnl2 splicing results in dual functions in neuronal cell survival and maintenance of cell integrity", Hum Mol Genet. May 15, 2012;21(10):2298-311. doi: 10.1093/hmg/dds050. Epub Feb. 15, 2012.PMID: 22343139.
Lambard et al., "Expression of rod-derived cone viability factor: dual role of CRX in regulating promoter activity and cell-type specificity", PLoS One. Oct. 7, 2010;5(10):e13075. doi: 10.1371/journal.pone.0013075.PMID: 20949100.
Arnau et al., "Current strategies for the use of affinity tags and tag removal for the purification of recombinant proteins," Protein Expression and Purification 48:1-13 (2006).
Berry et al., "Substitution of cysteine for selenocysteine in type I iodothyronine deiodinase reduces the catalytic efficiency of the protein but enhances its translation," Endocrinology 131(4):1848-1852 (1992).
Burns et al., "A high molecular weight-melanoma associated antigen-specific chimeric antigen receptor redirects lymphocytes to target human melanomas," Cancer Res. 70(8):3027-3033 (2010).
Chen et al., "Fusion Protein Linkers: Property, Design and Functionality," Adv Drug Deliv Rev. 65(10):1357-1369 (2013).
Gasser et al., "Antibody production with yeasts and filamentous fungi: on the road to large scale?" Biotechnol Lett. 29(2):201-212 (2007).
Kober et al., "Optimized Signal Peptides for the Development of High Expressing CHO Cell Lines," Biotechnol Bioeng. 110:1164-1173 (2013).
Maeda et al., "Engineering of functional chimeric protein G-Vargula luciferase," Analytical Biochemistry 249(2):147-152 (1997).
Muller et al., "Spliceosomal peptide P140 for immunotherapy of systemic lupus erythematosus: results of an early phase II clinical trial," Arthritis Rheum. 58(12):3873-3883 (2008).
Orlando, M. "Modification of proteins and low molecular weight substances with hydroxyethyl starch (HES)," Dissertation, Justus-Liebig-Universität Giessen, 2003.

* cited by examiner

M A S L F S G R I L I R N N S D Q D E L D T E A E V S R R L E N R
L V L L F F G A G A C P Q C Q A F V P I L K D F F V R L T D E F Y
V L R A A Q L A L V Y V S Q D S T E E Q Q D L F L K D M P K K W L
F L P F E D D L R R   (SEQ ID NO:5)

Figure 1A

M A S L F S G R I L I R N N S D Q D E L D T E A E V S R R L E N R
L V L L F F G A G A C P Q C Q A F V P I L K D F F V R L T D E F Y
V L R A A Q L A L V Y V S Q D S T E E Q Q D L F L K D M P K K W L
F L P F E D D L R R D L G R Q F S V E R L P A V V L K P D G D V
L T R D G A D E I Q R L G T A C F A N W Q E A A E V L D R N F Q L
P E D L E D Q E P R S L T E C L R R H K Y R V E K A A R G G R D P
G G G G G E E G G A G G L F   (SEQ ID NO:6)

FUSION PROTEIN BETWEEN SHORT FORM ROD-DERIVED CONE VIABILITY FACTOR AND A HYDROPHILIC PEPTIDE

REFERENCE TO SEQUENCE LISTING

The Sequence Listing filed electronically in the form of an Annex C/ST.25 text file and bearing file reference WOC-019PCT is a part of the disclosure.

BACKGROUND OF THE INVENTION

RdCVF is a thioredoxin-like protein specifically expressed by rod photoreceptor cells in the retina (Léveillard et al. (2004) Nature Genetics 36:755-759 and the supplemental information). Two different RdCVF genes are found in humans and they are designated RdCVF1 and RdCVF2. Both RdCVF genes encode two products via alternative splicing: a full length protein and a C-terminal post-transcriptionally truncated protein, known as RdCVF-long (RdCVFL) and RdCVF-short (RdCVFS), respectively. The nucleoredoxin-like-1 gene (Nxnl1) encodes a long and a short form RdCVF by alternative splicing mechanism. Nxnl1 knockout results in progressive loss of rods and cones in mice, suggesting at the genetic level this gene is fundamentally essential for survival of photoreceptor cells and maintaining proper retina physiology and function.

RdCVFS is described as a secreted trophic factor for promoting cone survival, and RdCVFL as a redox-active enzyme that interacts with intracellular proteins (Léveillard et al. (2010) Sci Transl Med. 2(26): 26ps16). For example, tau is described as a binding partner for RdCVF-L and tau is exclusively intracellular (Fridlich et al. (2009) Molecular & Cellular Proteomics 8(6):1206-18).

Individuals suffering from some retinal dystrophies were found to have lower levels of RdCVF protein in their eyes than did individuals without retinal dystrophies (PCT Publication WO 02/081513).

It has been demonstrated that different forms of RdCVF protein can promote cone photoreceptor cell survival in vitro and in vivo. For example, intraocular injections of the short form of human RdCVF1 (RdCVF1S) protein not only rescued cone cells from degeneration but also preserved their function in animal models of inherited retinal degeneration (Yang et al. (2009) Mol Therapy 17:787-795). However, demonstration of the in vivo cone cell protective effect of this protein required multiple intraocular injections.

Retinitis pigmentosa (RP) is retinal degenerative eye disease characterized by progressive rod degeneration followed by secondary loss of cones. RP is the leading cause of inherited blindness, affecting approximately 100,000 patients with 2,000 new cases per year in US alone. RP affects all ethnicities. More than 1.5 million people are affected by RP worldwide. Unfortunately for the patients, there is no effective therapy or approved therapy for RP. Therefore, RP remains an urgent unmet medical need.

Since RP is a chronic retinal degenerative disease with a clinical course over years to decades, gene therapy could be ideal for RP indication by expressing RdCVF in the retina constitutively. For acute emergency indications such as retinal detachment, protein therapy could be beneficial. That is to use recombinant RdCVF protein to protect photoreceptors from dying before the retina could be re-connected to the back of the eye, i.e., retinal pigment epithelium and choroid layers. Unfortunately, scientists in the field have encountered considerable difficulties to effectively express and secrete RdCVF protein, especially the short form RdCVF. See, for example, U.S. Patent Publication No. 20110034546, paragraph [0004].

SUMMARY OF THE INVENTION

This invention provides a fusion protein comprising a first N-terminal signal peptide sequence, a second peptide sequence C-terminal to the signal peptide sequence, and a third peptide sequence C-terminal to the second peptide sequence; wherein one of the second peptide sequence and the third peptide sequence is an RdCVF-short peptide sequence and the other is a hydrophilic peptide sequence. After translation the signal peptide is cleaved in the endoplasmic reticulum, leaving a fusion protein comprising the second peptide sequence and the third peptide sequence minus the signal peptide. Therefore this invention also provides a fusion protein comprising a second peptide sequence and a third peptide sequence C-terminal to the second peptide sequence; wherein one of the second peptide sequence and the third peptide sequence is an RdCVF-short peptide sequence and the other is a hydrophilic peptide sequence. This invention also provides nucleic acids and expression vectors encoding the fusion protein, cells comprising the nucleic acid or expression vector, as well as methods of treatment and uses of the fusion protein, nucleic acid, and expression vector. This invention also provides a method for producing the fusion protein comprising culturing the cells of this invention under conditions allowing for expression and secretion of the encoded fusion protein, and isolating the fusion protein from the cell culture.

BRIEF DESCRIPTION OF THE FIGURES

FIG. 2. Fusion protein between short RdCVF and hydrophilic domain.

FIG. 3. Expression and secretion of novel fusion proteins between human albumin and human short RdCVF.

Lane 1: 30 μL of cell culture medium from human 293 cells transduced with AAV-GFP, an AAV vector encoding GFP as a control;

Lane 2: 30 μL of cell culture medium from human 293 cells transduced with AAV-ALB-RdCVFS, an AAV vector encoding the short form human RdCVF fused with human albumin at the N-terminus of short RdCVF;

Lane 3: 30 μL of cell culture medium from human 293 cells transduced with AAV-RdCVFS-ALB, an AAV vector encoding the short form human RdCVF fused with human albumin at the C-terminus of short RdCVF.

The numbers on the left indicate molecular weight marker in KDa.

BRIEF DESCRIPTION OF THE SEQUENCE LISTING

SEQ ID NO: 1. Amino acid sequence of a fusion protein between human albumin and short RdCVF with human albumin at the N-terminus of the fusion protein (ALB-RdCVFS)

SEQ ID NO: 2. Nucleotide Sequence Encoding the Human Short RdCVF Fused with Human Albumin at N-terminus (ALB-RdCVFS)

SEQ ID NO: 3. Amino acid sequence of a fusion protein between human albumin and short RdCVF with human albumin at the C-terminus of the fusion protein (RdCVFS-ALB). There is a four amino acid spacer between RdCVFS and the human albumin. The first 21 amino acids from the N-terminus are signal sequence from mouse Igk. There is a 14 amino acid spacer (linker) between the signal sequence and RdCVFS.

SEQ ID NO:4. Nucleotide Sequence Encoding the Human Short RdCVF Fused with Human Albumin at C-terminus (RdCVFS-ALB)

SEQ ID NO: 5. Amino acid sequence of human short form rod-derived cone viability factor.

SEQ ID NO:6. Amino acid sequence of human long form rod-derived cone viability factor.

DETAILED DESCRIPTION OF THE INVENTION

Figure 1A:
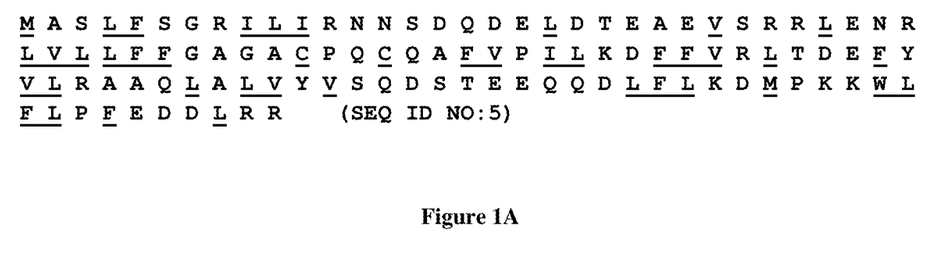
FIG. 1A shows amino acid sequence of human short form rod-derived cone viability factor. The amino acid composition for the human short RdCVF is highly hydrophobic. 38.5% of amino acids are hydrophobic in short RdCVF. Underlined amino acids are hydrophobic.
Figure 1B:
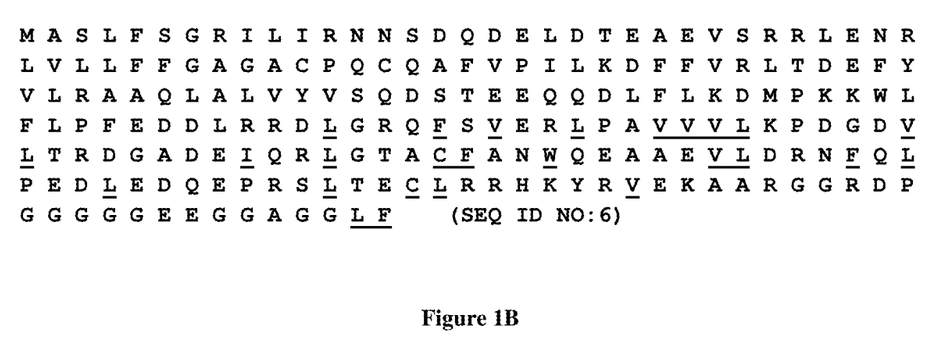
FIG. 1B shows amino acid sequence of human long form rod-derived cone viability factor. 25% of amino acids are hydrophobic at the C-terminus of long RdCVF (Underlined amino acids are hydrophobic at the C-terminus of the long form RdCVF)

Without wishing to be bound by theory, the difficulty to express and secrete the short form RdCVF could potentially be due to its high hydrophobic amino acid composition. Careful analysis of the amino acid composition of both the short form and the long form of human RdCVF proteins revealed that the short form RdCVF protein is extremely hydrophobic (FIGS. 1A and 1B). Forty two amino acids out of 109 (38.5%) are hydrophobic amino acids in short RdCVF. There is one stretch of six hydrophobic amino acids, one stretch of four hydrophobic amino acid, and two stretches of three hydrophobic amino acids each. It is highly likely that the high percentage of hydrophobic amino acid composition makes the short RdCVF very difficult to be expressed and secreted efficiently in vitro and in vivo from mammalian cells as it is more likely to stick to lipid membranes via hydrophobic-hydrophobic interactions. Interestingly, although the N-terminal 109 amino acids in the long form RdCVF are identical to the entire short RdCVF, the C-terminal 103 amino acids of the long RdCVF is not hydrophobic with only 25% of amino acids being hydrophobic (26 out of 103). The longest hydrophobic amino acids stretch in this C-terminus of the long RdCVF is only four amino acids long. There is no stretch of three hydrophobic amino acids. The relatively hydrophilic nature in the C-terminus of long RdCVF may play an important role in reducing the overall hydrophobicity of the long RdCVF.

In one embodiment of the fusion protein of this invention, the second peptide sequence is an RdCVF-short peptide sequence and the third peptide sequence is a hydrophilic peptide sequence. In another embodiment the second peptide sequence is a hydrophilic peptide sequence and the third peptide sequence is an RdCVF-short peptide sequence.

There should be an N-terminal signal peptide sequence that will facilitate the secretion of the fusion protein out of the cells that express this fusion protein. Any signal peptide that enables the secretion of a protein from mammalian cells can be utilized. In further embodiments, the signal peptide sequence is selected from the group consisting of an Igk signal peptide sequence and an albumin signal peptide sequence. In more specific embodiments the IgK signal peptide sequence is a mouse IgK signal peptide sequence and the albumin signal peptide sequence is a human albumin signal peptide sequence.

In a preferred embodiment of this invention the RdCVF-short peptide sequence is a human RdCVF-short peptide sequence. Examples of suitable RdCVF-short peptide sequences include an RdCVF1-short peptide sequence, an RdCVF2-short peptide sequence, and an RdCVF-short peptide sequence that differs from a corresponding wild-type sequence, for example by one or more conservative amino acid substitutions.

In accordance with this invention any hydrophilic peptide sequence can be utilized provided that lowers the hydrophobicity index of the fusion protein compared to the RdCVF-short peptide sequence without the hydrophilic peptide sequence. In one embodiment of this invention the fusion protein, including any signal peptide sequence if present, has a hydrophobicity index less than negative 0.20, more preferably less than negative 0.30.

Preferably the hydrophilic peptide sequence is not immunogenic in humans, does not present any other negative effect on human retinal physiology or normal retinal function, and does not affect short RdCVF's biological function. The hydrophilic peptide sequence can be a hydrophilic protein, a hydrophilic protein domain, a hydrophilic oligopeptide, or a hydrophilic polypeptide. More than one hydrophilic domain can be the candidate as the hydrophilic fusion partner with short RdCVF. In one embodiment of this invention the hydrophilic peptide sequence is an albumin, for example a human albumin.

In accordance with the fusion protein of this invention there can optionally be a spacer of one or more amino acids between the first peptide sequence and the second peptide sequence, between the second peptide sequence and the third peptide sequence, or both. In one embodiment of this invention there is no spacer between the first peptide sequence and the second peptide sequence, or in other words the first peptide sequence is covalently bonded to the second peptide sequence by a single peptide bond. In another embodiment there is a spacer between the first peptide sequence and the second peptide sequence. In another embodiment of this invention there is no spacer between the second peptide sequence and the third peptide sequence, or in other words the second peptide sequence is covalently bonded to the third peptide sequence by a single peptide bond. In another embodiment there is a spacer between the second peptide sequence and the third peptide sequence. There is in principle no limitation on the size of the spacers. In an embodiment of this invention the spacer between the first and second peptide sequence has two to fourteen amino acids. In another embodiment the spacer between the second and third peptide sequences has from two to fourteen amino acids, more specifically between two and four amino acids.

One embodiment of the fusion protein coding sequence of this invention further comprises a polyadenylation signal C-terminal to the third peptide sequence coding sequence. The polyadenylation signal (Poly A) can be any Poly A.

In one embodiment of the fusion protein of this invention, the first peptide sequence is a human albumin signal sequence, the second peptide sequence is a human albumin, and the third peptide sequence is an RdCVF-short sequence. In a more specific embodiment the fusion protein has the sequence (SEQ ID NO:1) or amino acids 25-717 of (SEQ ID NO:1). In another embodiment of the fusion protein of this invention the first peptide sequence is an Igk signal sequence, the second peptide sequence is an RdCVF-short sequence, and the third peptide sequence is a human albumin. In a more specific embodiment the fusion protein has the sequence (SEQ ID NO:3) or amino acids 22-732 of (SEQ ID NO:3).

In an embodiment of the fusion protein of this invention, wherein one, two, or all of the signal peptide sequence, the RdCVF-short peptide sequence, and the hydrophilic peptide sequence differs from a corresponding wild-type sequence. In a more specific embodiment the differences comprise one or more conservative amino acid substitutions. And in a still more specific embodiment the amino acid substitutions are limited one or more conservative amino acid substitutions.

The fusion protein in accordance with this invention can be glycosylated or not glycosylated. Generally speaking, glycosylation is beneficial for a protein's stability and solubility. In one embodiment the fusion protein expressed in cells transduced by an expression vector in accordance with this invention is glycosylated and is glycosylated after secretion from the cells.

In an embodiment the nucleic acid of this invention is DNA. In another embodiment the coding sequence for one, two, or all of the signal peptide sequence, the RdCVF-short peptide sequence and the hydrophilic peptide sequence is recoded compared to a corresponding wild-type sequence. In a more specific embodiment the coding sequence for the RdCVF-short peptide sequence is recoded. The nucleic acid of this invention can optionally comprise one or more introns, either between the first and the second peptide sequences, between the second and third peptide sequences, or elsewhere. In one embodiment of this invention the nucleic acid encodes a fusion protein having the sequence (SEQ ID NO:1), for example a nucleic acid having the sequence (SEQ ID NO:2). In another embodiment the nucleic acid encodes a fusion protein having the sequence (SEQ ID NO:3), for example a nucleic acid having the sequence (SEQ ID NO:4). Other nucleic acid sequences can readily be envisioned in view of the degeneracy of the genetic code.

An embodiment of this invention is an expression vector comprising the nucleic acid described above operatively linked to a control sequence, for example a promoter. The promoter driving the RdCVFS fusion protein can be any promoter and is not limited to CMV promoter. When there is an intron between the promoter and the fusion protein coding sequence, any suitable and conventional intron can be utilized. For example, (3-globin intron is suitable.

Figure 2:
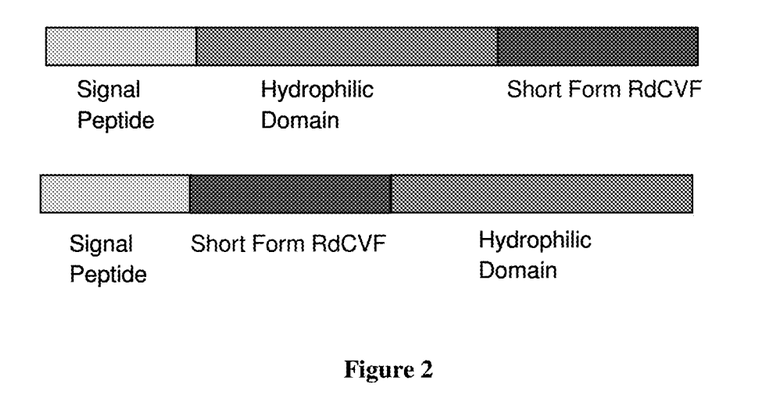
FIG. 2 shows schematic representations of two human short RdCVF fusion proteins. Human short RdCVF is fused with a hydrophilic domain at its N-terminus or C-terminus. The fusion protein has a signal peptide to facilitate secretion from cells.

In the experiments two fusion proteins were created by fusing human short RdCVF with a hydrophilic domain (See FIG. 2 for schematic). One was human short RdCVF fused with human albumin at the N-terminus with an albumin signal peptide at the N-terminus of the fusion protein (SEQ ID NO:1). The expression construct to express and secrete this fusion protein was engineered in the context of an AAV vector, designated rAAV-ALB-RdCVFS. This vector encoded a codon-optimized (recoded) human short RdCVF fused with human albumin at the N-terminus (SEQ ID NO:2). The fusion protein was named ALB-RdCVFS. A coding sequence for human albumin signal peptide was also incorporated into the fusion protein expression construct upstream of the fusion protein coding sequence. The expression construct further contained a CMV promoter and an intron that linked to the fusion protein coding sequence. The expression construct further contained a polyadenylation signal at the C-terminus of the fusion protein coding sequence. The entire expression cassette was cloned into an AAV expression plasmid and the plasmid was subjected to DNA sequencing to confirm the integrity of the expression construct.

The other exemplified fusion protein was human short RdCVF fused with human albumin at the C-terminus with a mouse Igk signal peptide at the N-terminus of the fusion protein (SEQ ID NO:3). The expression construct to express and secrete this fusion protein was engineered in the context of an AAV vector, designated rAAV-RdCVFS-ALB. This vector encoded a codon-optimized (recoded) human short RdCVF fused with human albumin at the C-terminus (SEQ ID NO:4). The fusion protein was named RdCVFS-ALB. A coding sequence for a modified mouse Igk signal peptide was also incorporated into the fusion protein expression construct upstream of the fusion protein coding sequence. The expression construct further contained a CMV promoter and an intron that linked to the fusion protein coding sequence. The expression construct further contained a polyadenylation signal at the C-terminus of the fusion protein coding sequence. The entire expression cassette was cloned into an AAV expression plasmid and the plasmid was subjected to DNA sequencing to confirm the integrity of the expression construct.

There are a total of 20 naturally-occurring amino acids. Some of them are hydrophobic and some of them are hydrophilic. The hydrophobicity index of an amino acid is a number representing the hydrophobic or hydrophilic properties of its sidechain. The larger the number is, the more hydrophobic the amino acid (Table 1). The most hydrophobic amino acids are isoleucine (4.5) and valine (4.2). The most hydrophilic ones are arginine (−4.5) and lysine (−3.9). Although a protein's hydrophobic or hydrophilic nature depends on what amino acids it is made of, as well as the secondary, tertiary and quaternary structure, the hydrophobicity index of a protein can have predictive value for a protein's hydrophobicity.

Table 1. Hydrophobicity Value of Amino Acids
Ala: 1.800
Arg: −4.500
Asn: −3.500
Asp: −3.500
Cys: 2.500
Gln: −3.500
Glu: −3.500
Gly: −0.400
His: −3.200
Ile: 4.500
Leu: 3.800
Lys: −3.900
Met: 1.900
Phe: 2.800
Pro: −1.600
Ser: −0.800
Thr: −0.700
Trp: −0.900
Tyr: −1.300
Val: 4.200

The publicly-available GPMAW program was used to calculate the hydrophobicity index for the short RdCVF, and the two short RdCVF and albumin fusion proteins. The hydrophobicity index for the native short form of human RdCVF (RdCVFS) is −0.12. After fusing the human albumin to the N-terminus of RdCVFS, the resulting fusion protein, ALB-RdCVFS had its hydrophobicity index reduced from −0.12 to −0.32 (including the signal peptide), a 266.7% reduction in hydrophobicity index. After fusing the human albumin to the C-terminus of RdCVFS, the resulting fusion protein, RdCVFS-ALB had its hydrophobicity index reduced from −0.12 to −0.33 (including the signal peptide), a 275% decrease in hydrophobicity index. The dramatic reduction in hydrophobicity index may have contributed to efficient expression and secretion of the fusion proteins.

Figure 3:
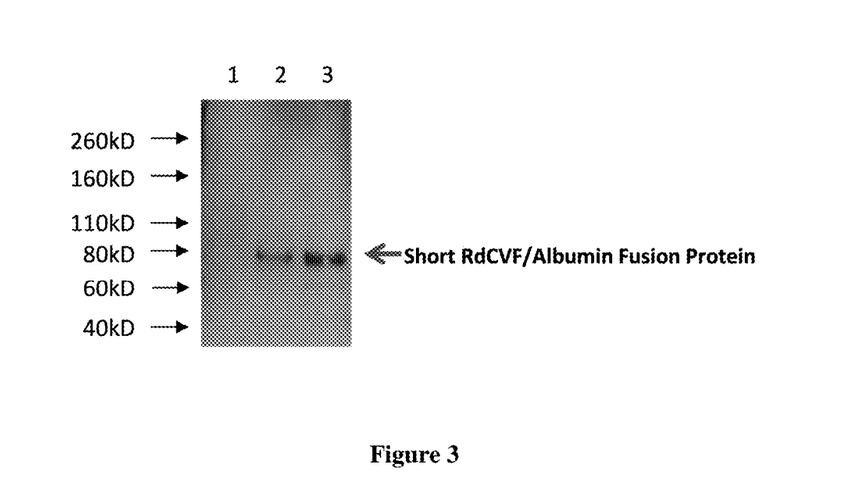
FIG. 3 shows a Western blot analysis of human short RdCVF and human albumin fusion proteins.

Furthermore, the fusion protein coding sequence has been cloned into an AAV-2 expression construct, the data included here clearly showed that this novel fusion protein was efficiently expressed as detected by Western blot with RdCVF specific antibodies (FIG. 3). The fusion partner for the short RdCVF is not limited to human albumin. Any hydrophilic protein or hydrophilic protein domain or hydrophilic peptide could be used to create a fusion protein with short RdCVF to reduce the protein's hydrophobicity. A preferred hydrophilic domain is non-immunogenic to human.

The protein can be encoded and delivered by a gene therapy vector such as AAV (Adeno-associated Virus) vector, Lentiviral vector, synthetic vector, adenoviral vector, retroviral vector, naked DNA, nanoparticles, etc. Alternatively, the fusion protein can be delivered to the retina as a recombinant protein. The hydrophilic fusion domain should not present any negative effect on human retinal physiology or normal retinal function, and should not affect short RdCVF's biological function. Potentially, more than one hydrophilic domain can be the candidate as the hydrophilic fusion partner with short RdCVF. In the examples, human albumin was used as the hydrophilic domain to serve as a fusion partner for human short RdCVF.

This invention provides a pharmaceutical composition comprising: (i) a component selected from the group consisting of a fusion protein, nucleic acid, expression vector, or cell of this invention; and (ii) a pharmaceutically acceptable carrier.

This invention provides a method for treating a condition amenable to such treatment in a mammalian patient, the treatment comprising administering to the patient an effective amount of the protein, the nucleic acid, the vector, the cell, or the pharmaceutical composition described herein, thereby treating the condition in the patient. In embodiments of this invention the condition is selected from the group consisting of retinal dystrophy, Stargardt's disease, retinitis pigmentosa, dry age-related macular degeneration (dry AMD), geographic atrophy (advanced stage of dry AMD), wet age-related macular degeneration (wet AMD), glaucoma with or without ocular hypertension, diabetic retinopathy, Bardet-Biedel syndrome, Bassen-Kornzweig syndrome, Best disease, choroidema, gyrate atrophy, congenital amaurosis, refsun syndrome, Usher syndrome, thyroid related eye disease, Grave's disease, a disease associated with retinal pigmented epithelial cells, anterior segment disease, lens disease/cataracts, an eye cup disorder, uveitis, Alzheimer's disease, Huntington's disease, Parkinson's disease, and an olfactory disease. Any conventional route of administration can be utilized, for example, injection to the eye, intravenous injection, or other systemic administration. In an embodiment of the method of this invention the condition is an ocular condition and the administration is selected from the group consisting of subretinal injection and intravitreal injection. In a more specific embodiment the patient is a human patient.

This invention provides a method of protecting ocular photoreceptor cells in a patient, comprising administering to the eye of the patient an effective amount of the fusion protein, nucleic acid, vector, cells, or pharmaceutical composition of this invention, thereby protecting the ocular photoreceptor cells in the patient. In a more specific embodiment the administration is selected from the group consisting of subretinal injection and intravitreal injection. In a more specific embodiment the patient is a human patient.

The invention is now described with reference to the following examples. These examples are provided for the purpose of illustration only and the invention should in no way be construed as being limited to these examples but rather should be construed to encompass any and all variations which become evident as a result of the teachings provided herein.

Whereas, particular embodiments of the invention have been described herein for purposes of description, it will be appreciated by those skilled in the art that numerous variations of the details may be made without departing from the invention as described in the appended claims.

All publications, patents and patent applications mentioned in this specification are herein incorporated by reference in their entirety into the specification to the same extent as if each individual publication, patent or patent application was specifically and individually indicated to be incorporated herein by reference. Also incorporated by reference is any supplemental information that was published along with any of the aforementioned publications, patents and patent applications. For example, some journal articles are published with supplemental information that is typically available online.

EXAMPLES

Example 1: Generation of rAAV Vectors Encoding Human Short Form Rod-Derived Cone Viability Factor and Albumin Fusion Proteins Plasmid Cloning The cDNA of the codon-optimized human short form of the RdCVF protein fused with human albumin at it N-terminus was synthesized by GENEART® (a fee-for-service company) and cloned into the adeno-associated virus vector plasmid pAAV-MCS (Cell Biolabs, San Diego, CA), creating the plasmid pAAV-ALB-RdCVFS. The signal peptide from human albumin was also incorporated at the upstream of the RdCVF and albumin fusion protein coding sequence.

The pAAV-ALB-RdCVFS plasmid contains the following features between AAV-ITRs:

CMV promoter-β-globin intron-Signal sequence-Albumin-short RdCVF-Poly A

The resulting amino acid sequence for this RdCVF and albumin fusion protein is shown in SEQ ID NO: 1.

The cDNA of the codon-optimized human short form of the RdCVF protein fused with human albumin at it C-terminus was synthesized by GENEART® (a fee-for-service company) and cloned into the adeno-associated virus vector plasmid pAAV-MCS (Cell Biolabs, San Diego, CA), creating the plasmid pAAV-RdCVFS-ALB. This signal peptide from mouse Igk was also incorporated at the upstream of the RdCVF and albumin fusion protein coding sequence.

The pAAV-RdCVFS-ALB plasmid contains the following features between AAV-ITRs:

CMV promoter-β-globin intron-Signal sequence-short RdCVF-Albumin-Poly A

The resulting amino acid sequence for this RdCVF and albumin fusion protein is shown in SEQ ID NO: 3.

Production and Purification of Recombinant AAV-ALB-RdCVFS and AAV-RdCVFS-ALB Vectors Plasmids pAAV-ALB-RdCVFS or pAAV-RdCVFS-ALB, pHELPER (Cell BioLabs, Catalog No. 340202), and pRC2 (Cell BioLabs, Catalog No. 340201) were transformed into DH10B competent bacteria cells (Invitrogen, Catalog No. 18297-010) and scaled up using the Qiagen EndoFree Plasmid Maxi Kit or EndoFree Plasmid Mega Kit according to the manufacturer's instructions. The plasmid concentrations were determined using a Beckman DU-600 spectrophotometer. Each plasmid's identity was confirmed by restriction digests and DNA sequencing analysis.

To produce rAAV-ALB-RdCVFS or rAAV-RdCVFS-ALB vector, 293AAV cells (Cell BioLabs, Catalog No. AAV-100) were seeded at 4 million cells per 15 cm dish in cDMEM (DMEM supplemented with 10% FBS, 1% Glutamine, 1% non-essential amino acids, and 1% Penicillin/Streptomycin). The following day the medium was replaced with 25 mL fresh cDMEM. Two hours later the transfection was performed. Water (57.4 mL) was mixed with 1.3 mg pHELPER, 650 µg pRC2, 650 µg pAAV-ALB-RdCVFS or pAAV-RdCVFS-ALB, and 8.1 mL 2 M $CaCl_2$ (water/plasmid/$CaCl_2$ mix). A 12.5 mL volume of 2×HBS (Lonza, Sku:RR07005) was transferred into each of five 50 mL conical tubes. While vortexing, 12.5 mL of the water/plasmid/$CaCl_2$ mix was slowly added to each of the conical tubes containing 2×HBS. After a 5-minute incubation, 2.5 mL of the suspension was added to each cell culture dish containing the 293AAV cells.

The following day the medium was replaced with 25 mL new cDMEM medium per dish. Two days later the cells were harvested using a cell lifter and the cell/medium mix was transferred into 250 mL conical tubes. The samples were centrifuged at 3,000 rpm for 15 minutes at 4° C., the supernatant was discarded and the cell pellets resuspended in 110 mL DMEM. The resuspended cell samples were aliquoted (30 mL) into 50 mL conical tubes and a freeze/thaw/freeze step was performed using ethanol/dry ice bath and 37° C. water bath. The tubes were stored at −80° C. until further process of the material. The same process was employed to produce rAAV-GFP control vector, substituting the plasmid pAAV-ALB-RdCVFS with the plasmid pAAV-GFP (Cell BioLabs Catalog No. AAV-400).

To purify the rAAV-ALB-RdCVFS vector, four 50 mL conical tubes containing the vector from the freeze/thaw/freeze step was thawed at 37° C. in a water bath. Forty microliters of BENZONASE® (nuclease) (Sigma, Catalog No. E8263-25kU) was added to each tube which was then incubated at 37° C. for 30 minutes. The tubes were centrifuged for 10 minutes at 3,000 rpm and the supernatants were transferred into a 500 mL bottle. Six milliliters of a 10% sodium deoxycholate solution (8.2 g in 82 mL water) was added. The sample was briefly mixed and incubated at 37° C. for 30 minutes. The suspension was filtered using 5 µm filters. Subsequently, another filtration step using 0.8 µm filter was performed. A heparin agarose column (8 mL) (Sigma, Catalog No. H6508-25 mL) was prepared and the column was equilibrated with 48 mL phosphate buffered saline (PBS) (Invitrogen, Catalog No. 10010-049). The filtered cell lysate was loaded onto the column and the column was washed with 40 mL washing buffer (20 mL 5 M NaCl, 980 mL PBS). The vector was eluted using 15 mL elution buffer (80 mL 5 M NaCl, 920 mL PBS) and collected in a new 50 mL conical tube.

The vector was concentrated by centrifugal filtration. An AMICON ULTRA-15 centrifugational filter unit (Millipore, Catalog No. UFC910024) was rinsed once with PBS and the eluted sample was added to the device. Centrifugation was performed in a Beckman Allegro 6KR centrifuge at 2,200 rpm, 22° C., until the sample was concentrated to a 1-2 mL volume. A 15 mL volume of PBS was added and the centrifugation was repeated until the sample volume was <1 mL. The purified vector was collected and the filter walls rinsed with 100 µL of PBS. The sample was mixed and 30 µL aliquots of the vector were stored at −80° C. in 600 µL conical tubes until use.

This process was repeated to purify the rAAV-RdCVFS-ALB and rAAV-GFP vectors.

Example 2: Expression and Secretion of Human Short RdCVF and Human Albumin Fusion Proteins Mediated by rAAV Vectors Western blot analysis using a 4-20% SDS-PAGE gel was used to detect RdCVF and albumin fusion protein expression using standard techniques. As a control, a 5 µL volume of MAGICMARK™ XP Western Protein Standard (Invitrogen, Catalog No. LC5602) was added to the outer wells. 30 µL of cell culture medium from each rAAV vector transduced human 293 cells mixed with protein sample buffer was added to each well. The gel was run at 200 V until the dye reached the bottom of the gel. Western blot analysis was performed with a VECTASTAIN® ABC-Amp Western blot analysis kit by Vector Laboratories, according to a modified version of the manufacturer's instructions. The SDS-PAGE was equilibrated in transfer buffer for 20 min and proteins separated by SDS-PAGE were transferred onto a nitrocellulose membrane using a Trans Blot Semi-Dry Transfer Cell at 20 V for 40 minutes. Once the transfer was completed, the membrane was blocked in 200 mL of 1× casein solution with gentle agitation on a rocker platform for at least two hours at room temperature (RT) or at 4° C. overnight. The membrane was incubated with 50 mL 1× casein solution containing rabbit anti-RdCVF protein specific antibody (primary antibody, generated by Covance (Denver, PA) diluted 1:2,000 with gentle agitation at 4° C. overnight or 1 hour at room temperature. The membrane was washed with 30 mL of a 1× casein solution 4 times for 5 minutes each at RT with gentle agitation. The membrane was incubated with 30 mL of biotinylated goat anti-rabbit IgG (secondary antibody) diluted 1:10,000 in 1× casein solution for 1 hour at RT with gentle agitation. The membrane was washed in 30 mL of 1× casein solution 3 times for 5 minutes each at RT with gentle agitation. The membrane was incubated for 45 minutes in Vectastain ABC-AmP in 50 mL of 1× casein containing 100 µL of Reagent A and 100 µL of Reagent B. The membrane was washed in 30 mL of 1× casein solution 3 times for 5 minutes each at RT with gentle agitation.

The membrane was incubated in Tris, pH 9.5. The chemiluminescent signal was acquired using 6 mL of DUOLOX Substrate (Vector Laboratories, Catalog No. SK 6605) and exposing the membrane to KODAK BIOMAX MS X-ray film (Kodak Carestream Health, Catalog No. 8572786) in a film cassette for 10 seconds to 5 minutes followed by development of the film using KODAK Developer solution (Kodak GBX, Catalog No. 1900984) and KODAK Fixer solution.

As shown in FIG. 3, cell culture medium from both rAAV-ALB-RdCVFS and rAAV-RdCVFS-ALB transduced human 293 cells contained a band at molecular weight approximately 80 KDa that specifically reacted with rabbit anti-RdCVF antibodies. This band was not detected in the cell culture medium from rAAV-GFP control vector transduced cells. The data suggest both rAAV-ALB-RdCVFS and rAAV-RdCVFS-ALB vectors mediated human short RdCVF and albumin fusion protein expression and secretion in human cells.

The rAAV-ALB-RdCVFS or rAAV-RdCVFS-ALB vectors can be used for intraocular administration to treat the diseases listed above. Specifically, the vectors can be delivered via subretinal injection or intravitreal injection.

SUMMARY

The recombinant AAV vector encoding a codon-optimized (recoded) human short RdCVF fused with human albumin fusion protein coding sequence at its N-terminus was able to mediate the fusion protein expression in and secretion from human cells. The recombinant AAV vector encoding a codon-optimized human short RdCVF fused with human albumin fusion protein at its C-terminus was able to mediate the fusion protein expression in and secretion from human cells.

What is claimed is:

1. A method of protecting ocular photoreceptor cells in a patient, comprising administering to the eye of the patient an effective amount of an agent selected from one or more of:
   (i) a fusion protein comprising: (a) a first N-terminal signal peptide sequence, a second peptide sequence C-terminal to the signal peptide sequence, and a third peptide sequence C-terminal to the second peptide sequence; or (b) a second peptide sequence and a third peptide sequence C-terminal to the second peptide sequence; wherein the first peptide sequence is an Igk signal sequence, the second peptide sequence is an RdCVF-short sequence, and the third peptide sequence is a human albumin; and
   wherein the fusion protein comprises the sequence SEQ ID NO:3 or amino acids 22-732 of SEQ ID NO:3;
   (ii) a nucleic acid encoding the fusion protein of (i);
   (iii) an expression vector comprising the nucleic acid of (ii), operatively linked to a control sequence; and
   (iv) a cell comprising the nucleic acid of (ii) or the expression vector of (iii),
   thereby protecting the ocular photoreceptor cells in the patient.

2. The method of claim 1, wherein the agent is the fusion protein.

3. The method of claim 1, wherein the agent is the nucleic acid encoding the fusion protein.

4. The method of claim 3, wherein the nucleic acid comprises the sequence SEQ ID NO:4.

5. The method of claim 1, wherein the agent is the cell.

6. The method of claim 1, wherein the administration is selected from the group consisting of subretinal injection and intravitreal injection.

7. The method of claim 1, wherein the patient is a human patient.

8. The method of claim 1, wherein the agent is the expression vector.

9. The method of claim 1, wherein the agent is the fusion protein comprising the sequence SEQ ID NO:3.

10. The method of claim 1, wherein the agent is the fusion protein comprising amino acids 22-732 of SEQ ID NO:3.

* * * * *

SEQUENCE LISTING

```
<160> NUMBER OF SEQ ID NOS: 6

<210> SEQ ID NO 1
<211> LENGTH: 717
<212> TYPE: PRT
<213> ORGANISM: Homo sapiens
<220> FEATURE:
<221> NAME/KEY: SIGNAL
<222> LOCATION: (1)..(24)
<223> OTHER INFORMATION: Signal sequence from human albumin
<220> FEATURE:
<221> NAME/KEY: MISC_FEATURE
<222> LOCATION: (1)..(609)
<223> OTHER INFORMATION: Human albumin (including N-terminal signal
      peptide)
<220> FEATURE:
<221> NAME/KEY: MISC_FEATURE
<222> LOCATION: (25)..(609)
<223> OTHER INFORMATION: Human albumin (excluding N-terminal signal
      peptide)
<220> FEATURE:
<221> NAME/KEY: MISC_FEATURE
<222> LOCATION: (610)..(717)
<223> OTHER INFORMATION: RdCVFS

<400> SEQUENCE: 1

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190
```

```
Cys Gln Ala Ala Asp Lys Ala Ala Cys Leu Leu Pro Lys Leu Asp Glu
    195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                     230                 235                 240

Ala Arg Leu Ser Gln Arg Phe Pro Lys Ala Glu Phe Ala Glu Val Ser
                    245                 250                 255

Lys Leu Val Thr Asp Leu Thr Lys Val His Thr Glu Cys Cys His Gly
                260                 265                 270

Asp Leu Leu Glu Cys Ala Asp Asp Arg Ala Asp Leu Ala Lys Tyr Ile
                275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                     310                 315                 320

Glu Met Pro Ala Asp Leu Pro Ser Leu Ala Ala Asp Phe Val Glu Ser
                    325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
                355                 360                 365

Leu Leu Leu Arg Leu Ala Lys Thr Tyr Glu Thr Thr Leu Glu Lys Cys
            370                 375                 380

Cys Ala Ala Ala Asp Pro His Glu Cys Tyr Ala Lys Val Phe Asp Glu
385                     390                 395                 400

Phe Lys Pro Leu Val Glu Glu Pro Gln Asn Leu Ile Lys Gln Asn Cys
                    405                 410                 415

Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                     470                 475                 480

Leu Asn Gln Leu Cys Val Leu His Glu Lys Thr Pro Val Ser Asp Arg
                    485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                     550                 555                 560

Pro Lys Ala Thr Lys Glu Gln Leu Lys Ala Val Met Asp Asp Phe Ala
                    565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
            595                 600                 605
```

```
Leu Ala Ser Leu Phe Ser Gly Arg Ile Leu Ile Arg Asn Asn Ser Asp
            610                 615                 620

Gln Asp Glu Leu Asp Thr Glu Ala Glu Val Ser Arg Arg Leu Glu Asn
625                 630                 635                 640

Arg Leu Val Leu Phe Phe Gly Ala Gly Ala Cys Pro Gln Cys Gln
                645                 650                 655

Ala Phe Val Pro Ile Leu Lys Asp Phe Phe Val Arg Leu Thr Asp Glu
                660                 665                 670

Phe Tyr Val Leu Arg Ala Ala Gln Leu Ala Leu Val Tyr Val Ser Gln
            675                 680                 685

Asp Ser Thr Glu Glu Gln Gln Asp Leu Phe Leu Lys Asp Met Pro Lys
            690                 695                 700

Lys Trp Leu Phe Leu Pro Phe Glu Asp Asp Leu Arg Arg
705                 710                 715

<210> SEQ ID NO 2
<211> LENGTH: 2154
<212> TYPE: DNA
<213> ORGANISM: Homo sapiens

<400> SEQUENCE: 2
atgaagtggg taaccttat ttcccttctt tttctcttta gctcggctta ttccaggggt     60
gtgtttcgtc gagatgcaca caagagtgag gttgctcatc ggtttaaaga tttgggagaa    120
gaaaatttca agccttggt gttgattgcc tttgctcagt atcttcagca gtgtccattt     180
gaagatcatg taaaattagt gaatgaagta actgaatttg caaaaacatg tgttgctgat    240
gagtcagctg aaaattgtga caaatcactt cataccctt ttggagacaa attatgcaca     300
gttgcaactc ttcgtgaaac ctatggtgaa atggctgact gctgtgcaaa acaagaacct    360
gagagaaatg aatgcttctt gcaacacaaa gatgacaacc caaacctccc ccgattggtg    420
agaccagagg ttgatgtgat gtgcactgct tttcatgaca tgaagagaca ttttttgaaa    480
aaatacttat atgaaattgc cagaagacat ccttactttt atgccccgga actccttttc    540
tttgctaaaa ggtataaagc tgcttttaca gaatgttgcc aagctgctga taagctgcc     600 tgcctgttgc caaagctcga tgaacttcgg gatgaaggga aggcttcgtc tgccaaacag    660
agactcaagt gtgccagtct ccaaaaattt ggagaagag ctttcaaagc atgggcagta     720
gctcgcctga ccagagatt tcccaaagct gagtttgcag aagtttccaa gttagtgaca    780
gatcttacca agtccacac ggaatgctgc catggagatc tgcttgaatg tgctgatgac     840
agggcggacc ttgccaagta tatctgtgaa atcaagatt cgatctccag taaactgaag     900
gaatgctgtg aaaaacctct gttggaaaaa tcccactgca ttgccgaagt ggaaaatgat    960
gagatgcctg ctgacttgcc ttcattagct gctgattttg ttgaaagtaa ggatgtttgc   1020
aaaaactatg ctgaggcaaa ggatgtcttc ctgggcatgt ttttgtatga atatgcaaga   1080
aggcatcctg attactctgt cgtgctgctg ctgagacttg ccaagacata tgaaaccact   1140
ctagagaagt gctgtgccgc tgcagatcct catgaatgct atgccaaagt gttcgatgaa   1200
tttaaacctc ttgtggaaga gcctcagaat ttaatcaaac aaaattgtga gcttttgag    1260 cagcttggag agtacaaatt ccagaatgcg ctattagttc gttacaccaa gaaagtaccc   1320
caagtgtcaa ctccaactct tgtagaggtc tcaagaaacc taggaaagt gggcagcaaa   1380 tgttgtaaac atcctgaagc aaaaagaatg ccctgtgcag aagactatct atccgtggtc   1440
ctgaaccagt tatgtgtgtt gcatgagaaa acgccagtaa gtgacagagt caccaaatgc   1500
```

-continued

```
tgcacagaat ccttggtgaa caggcgacca tgcttttcag ctctggaagt cgatgaaaca    1560
tacgttccca aagagtttaa tgctgaaaca ttcaccttcc atgcagatat atgcacactt    1620
tctgagaagg agagacaaat caagaaacaa actgcacttg ttgagctcgt gaaacacaag    1680
cccaaggcaa caaagagca actgaaagct gttatggatg atttcgcagc ttttgtagag     1740
aagtgctgca aggctgacga taaggagacc tgctttgccg aggagggtaa aaaacttgtt    1800
gctgcaagtc aagctgcctt aggcttagcc agcctgttca gcggccggat cctgatcagg    1860
aacaacagcg accaggacga gctggacacc gaggccgaag tgagcaggag gctggagaac    1920
agactggtgc tgctgttctt tggcgccgga gcctgccctc agtgccaggc cttcgtgccc    1980
atcctgaagg atttctttgt gcggctgacc gacgagttct acgtgctgag agccgcccag    2040
ctggccctgg tgtatgtgag ccaggacagc accgaggagc agcaggacct gttcctgaag    2100
gacatgccca agaagtggct gttcctgccc ttcgaggacg acctgcggag atga           2154
```

<210> SEQ ID NO 3
<211> LENGTH: 732
<212> TYPE: PRT
<213> ORGANISM: Artificial Sequence
<220> FEATURE:
<223> OTHER INFORMATION: N-terminal signal sequence from mouse IgK,
      followed by spacer, followed by RdCVFS, followed by spacer,
      followed by human albumin at C-terminus.
<220> FEATURE:
<221> NAME/KEY: SIGNAL
<222> LOCATION: (1)..(21)
<223> OTHER INFORMATION: Signal sequence from mouse Igk.
<220> FEATURE:
<221> NAME/KEY: MISC_FEATURE
<222> LOCATION: (22)..(35)
<223> OTHER INFORMATION: Spacer
<220> FEATURE:
<221> NAME/KEY: MISC_FEATURE
<222> LOCATION: (36)..(143)
<223> OTHER INFORMATION: RdCVFS
<220> FEATURE:
<221> NAME/KEY: MISC_FEATURE
<222> LOCATION: (144)..(147)
<223> OTHER INFORMATION: Spacer
<220> FEATURE:
<221> NAME/KEY: MISC_FEATURE
<222> LOCATION: (148)..(732)
<223> OTHER INFORMATION: Human albumin

<400> SEQUENCE: 3

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Val Arg Ser
            20                  25                  30

Leu Val Pro Ala Ser Leu Phe Ser Gly Arg Ile Leu Ile Arg Asn Asn
        35                  40                  45

Ser Asp Gln Asp Glu Leu Asp Thr Glu Ala Glu Val Ser Arg Arg Leu
    50                  55                  60

Glu Asn Arg Leu Val Leu Leu Phe Phe Gly Ala Gly Ala Cys Pro Gln
65                  70                  75                  80

Cys Gln Ala Phe Val Pro Ile Leu Lys Asp Phe Phe Val Arg Leu Thr
                85                  90                  95

Asp Glu Phe Tyr Val Leu Arg Ala Ala Gln Leu Ala Leu Val Tyr Val
            100                 105                 110

Ser Gln Asp Ser Thr Glu Glu Gln Gln Asp Leu Phe Leu Lys Asp Met
        115                 120                 125
```

```
Pro Lys Lys Trp Leu Phe Leu Pro Phe Glu Asp Asp Leu Arg Arg Gly
130                 135                 140

Arg Asp Ala Asp Ala His Lys Ser Glu Val Ala His Arg Phe Lys Asp
145                 150                 155                 160

Leu Gly Glu Glu Asn Phe Lys Ala Leu Val Leu Ile Ala Phe Ala Gln
                165                 170                 175

Tyr Leu Gln Gln Cys Pro Phe Glu Asp His Val Lys Leu Val Asn Glu
            180                 185                 190

Val Thr Glu Phe Ala Lys Thr Cys Val Ala Asp Glu Ser Ala Glu Asn
        195                 200                 205

Cys Asp Lys Ser Leu His Thr Leu Phe Gly Asp Lys Leu Cys Thr Val
210                 215                 220

Ala Thr Leu Arg Glu Thr Tyr Gly Glu Met Ala Asp Cys Cys Ala Lys
225                 230                 235                 240

Gln Glu Pro Glu Arg Asn Glu Cys Phe Leu Gln His Lys Asp Asp Asn
                245                 250                 255

Pro Asn Leu Pro Arg Leu Val Arg Pro Glu Val Asp Val Met Cys Thr
                260                 265                 270

Ala Phe His Asp Asn Glu Glu Thr Phe Leu Lys Lys Tyr Leu Tyr Glu
        275                 280                 285

Ile Ala Arg Arg His Pro Tyr Phe Tyr Ala Pro Glu Leu Leu Phe Phe
290                 295                 300

Ala Lys Arg Tyr Lys Ala Ala Phe Thr Glu Cys Cys Gln Ala Ala Asp
305                 310                 315                 320

Lys Ala Ala Cys Leu Leu Pro Lys Leu Asp Glu Leu Arg Asp Glu Gly
                325                 330                 335

Lys Ala Ser Ser Ala Lys Gln Arg Leu Lys Cys Ala Ser Leu Gln Lys
                340                 345                 350

Phe Gly Glu Arg Ala Phe Lys Ala Trp Ala Val Ala Arg Leu Ser Gln
            355                 360                 365

Arg Phe Pro Lys Ala Glu Phe Ala Glu Val Ser Lys Leu Val Thr Asp
        370                 375                 380

Leu Thr Lys Val His Thr Glu Cys Cys His Gly Asp Leu Leu Glu Cys
385                 390                 395                 400

Ala Asp Asp Arg Ala Asp Leu Ala Lys Tyr Ile Cys Glu Asn Gln Asp
                405                 410                 415

Ser Ile Ser Ser Lys Leu Lys Glu Cys Cys Glu Lys Pro Leu Leu Glu
                420                 425                 430

Lys Ser His Cys Ile Ala Glu Val Glu Asn Asp Glu Met Pro Ala Asp
            435                 440                 445

Leu Pro Ser Leu Ala Ala Asp Phe Val Glu Ser Lys Asp Val Cys Lys
        450                 455                 460

Asn Tyr Ala Glu Ala Lys Asp Val Phe Leu Gly Met Phe Leu Tyr Glu
465                 470                 475                 480

Tyr Ala Arg Arg His Pro Asp Tyr Ser Val Val Leu Leu Leu Arg Leu
                485                 490                 495

Ala Lys Thr Tyr Glu Thr Thr Leu Glu Lys Cys Cys Ala Ala Ala Asp
                500                 505                 510

Pro His Glu Cys Tyr Ala Lys Val Phe Asp Glu Phe Lys Pro Leu Val
        515                 520                 525

Glu Glu Pro Gln Asn Leu Ile Lys Gln Asn Cys Glu Leu Phe Glu Gln
530                 535                 540
```

```
Leu Gly Glu Tyr Lys Phe Gln Asn Ala Leu Leu Val Arg Tyr Thr Lys
545                 550                 555                 560

Lys Val Pro Gln Val Ser Thr Pro Thr Leu Val Glu Val Ser Arg Asn
                565                 570                 575

Leu Gly Lys Val Gly Ser Lys Cys Cys Lys His Pro Glu Ala Lys Arg
            580                 585                 590

Met Pro Cys Ala Glu Asp Tyr Leu Ser Val Val Leu Asn Gln Leu Cys
        595                 600                 605

Val Leu His Glu Lys Thr Pro Val Ser Asp Arg Val Thr Lys Cys Cys
    610                 615                 620

Thr Glu Ser Leu Val Asn Arg Arg Pro Cys Phe Ser Ala Leu Glu Val
625                 630                 635                 640

Asp Glu Thr Tyr Val Pro Lys Glu Phe Asn Ala Glu Thr Phe Thr Phe
                645                 650                 655

His Ala Asp Ile Cys Thr Leu Ser Glu Lys Glu Arg Gln Ile Lys Lys
            660                 665                 670

Gln Thr Ala Leu Val Glu Leu Val Lys His Lys Pro Lys Ala Thr Lys
        675                 680                 685

Glu Gln Leu Lys Ala Val Met Asp Asp Phe Ala Ala Phe Val Glu Lys
    690                 695                 700

Cys Cys Lys Ala Asp Asp Lys Glu Thr Cys Phe Ala Glu Glu Gly Lys
705                 710                 715                 720

Lys Leu Val Ala Ala Ser Gln Ala Ala Leu Gly Leu
                725                 730
```

<210> SEQ ID NO 4
<211> LENGTH: 2199
<212> TYPE: DNA
<213> ORGANISM: Artificial Sequence
<220> FEATURE:
<223> OTHER INFORMATION: N-terminal signal sequence from mouse IgK,
      followed by spacer, followed by RdCVFS, followed by spacer,
      followed by human albumin at C-terminus.

<400> SEQUENCE: 4

```
atggagacag acacactcct gctatgggta ctgctgctct gggttccagg ttccactggt      60
gacgcggccc agccggccag gcgcgccgta cgaagcttgg tacccgccag cctgttcagc     120
ggccggatcc tgatcaggaa caacagcgac caggacgagc tggacaccga ggccgaagtg     180
agcaggaggc tggagaacag actggtgctg ctgttctttg gcgccggagc ctgccctcag     240
tgccaggcct tcgtgcccat cctgaaggat ttctttgtgc ggctgaccga cgagttctac     300
gtgctgagag ccgcccagct ggccctggtg tatgtgagcc aggacagcac cgaggagcag     360
caggacctgt tcctgaagga catgcccaag aagtggctgt tcctgccctt cgaggacgac     420
ctgcggagag acgagatgc agatgcacac aagagtgagg ttgctcatcg gtttaaagat     480
ttgggagaag aaaatttcaa agccttggtt tgattgcct tgctcagta tcttcagcag     540 tgtccatttg aagatcatgt aaaattagtg aatgaagtaa ctgaatttgc aaaaacatgt     600
gttgctgatg agtcagctga aaattgtgac aaatcacttc ataccctttt tggagacaaa     660
ttatgcacag ttgcaactct tcgtgaaacc tatggtgaaa tggctgactg ctgtgcaaaa     720
caagaacctg agagaaatga atgcttcttg caacacaaag atgacaaccc aaacctcccc     780
cgattggtga gaccagaggt tgatgtgatg tgcactgctt tcatgacaa tgaagagaca     840 tttttgaaaa aatacttata tgaaattgcc agaagacatc cttactttta tgcccggaa     900
```

-continued

```
ctccttttct tgctaaaag gtataaagct gcttttacag aatgttgcca agctgctgat    960
aaagctgcct gcctgttgcc aaagctcgat gaacttcggg atgaagggaa ggcttcgtct   1020
gccaaacaga gactcaagtg tgccagtctc caaaaatttg gagaaagagc tttcaaagca   1080
tgggcagtag ctcgcctgag ccagagattt cccaaagctg agtttgcaga gtttccaag    1140
ttagtgacag atcttaccaa agtccacacg gaatgctgcc atggagatct gcttgaatgt   1200
gctgatgaca gggcggacct tgccaagtat atctgtgaaa atcaagattc gatcccagt    1260
aaactgaagg aatgctgtga aaaacctctg ttggaaaaat cccactgcat tgccgaagtg   1320
gaaaatgatg agatgcctgc tgacttgcct tcattagctg ctgattttgt tgaaagtaag   1380
gatgtttgca aaactatgc tgaggcaaag gatgtcttcc tgggcatgtt tttgtatgaa    1440
tatgcaagaa ggcatcctga ttactctgtc gtgctgctgc tgagacttgc caagacatat   1500
gaaaccactc tagagaagtg ctgtgccgct gcagatcctc atgaatgcta tgccaaagtg   1560
ttcgatgaat ttaaacctct tgtggaagag cctcagaatt taatcaaaca aaattgtgag   1620
cttttttgagc agcttggaga gtacaaattc cagaatgcgc tattagttcg ttacaccaag   1680
aaagtacccc aagtgtcaac tccaactctt gtagaggtct caagaaacct aggaaaagtg   1740
ggcagcaaat gttgtaaaca tcctgaagca aaaagaatgc cctgtgcaga agactatcta   1800
tccgtggtcc tgaaccagtt atgtgtgttg catgagaaaa cgccagtaag tgacagagtc   1860
accaaatgct gcacagaatc cttggtgaac aggcgaccat gcttttcagc tctggaagtc   1920
gatgaaacat acgttcccaa agagtttaat gctgaaacat tcaccttcca tgcagatata   1980
tgcacacttt ctgagaagga gagacaaatc aagaaacaaa ctgcacttgt tgagctcgtg   2040
aaacacaagc ccaaggcaac aaaagagcaa ctgaaagctg ttatggatga tttcgcagct   2100
tttgtagaga agtgctgcaa ggctgacgat aaggagacct gctttgccga ggagggtaaa   2160
aaacttgttg ctgcaagtca agctgcctta ggcttataa                         2199
```

<210> SEQ ID NO 5
<211> LENGTH: 109
<212> TYPE: PRT
<213> ORGANISM: Homo sapiens

<400> SEQUENCE: 5

Met Ala Ser Leu Phe Ser Gly Arg Ile Leu Ile Arg Asn Asn Ser Asp
1               5                   10                  15

Gln Asp Glu Leu Asp Thr Glu Ala Glu Val Ser Arg Arg Leu Glu Asn
            20                  25                  30

Arg Leu Val Leu Leu Phe Phe Gly Ala Gly Ala Cys Pro Gln Cys Gln
        35                  40                  45

Ala Phe Val Pro Ile Leu Lys Asp Phe Phe Val Arg Leu Thr Asp Glu
    50                  55                  60

Phe Tyr Val Leu Arg Ala Ala Gln Leu Ala Leu Val Tyr Val Ser Gln
65                  70                  75                  80

Asp Ser Thr Glu Glu Gln Gln Asp Leu Phe Leu Lys Asp Met Pro Lys
                85                  90                  95

Lys Trp Leu Phe Leu Pro Phe Glu Asp Asp Leu Arg Arg
            100                 105

<210> SEQ ID NO 6
<211> LENGTH: 212
<212> TYPE: PRT
<213> ORGANISM: Homo sapiens

```
<400> SEQUENCE: 6

Met Ala Ser Leu Phe Ser Gly Arg Ile Leu Ile Arg Asn Asn Ser Asp
1               5                   10                  15

Gln Asp Glu Leu Asp Thr Glu Ala Glu Val Ser Arg Arg Leu Glu Asn
            20                  25                  30

Arg Leu Val Leu Leu Phe Phe Gly Ala Gly Ala Cys Pro Gln Cys Gln
            35                  40                  45

Ala Phe Val Pro Ile Leu Lys Asp Phe Phe Val Arg Leu Thr Asp Glu
    50                  55                  60

Phe Tyr Val Leu Arg Ala Ala Gln Leu Ala Leu Val Tyr Val Ser Gln
65                  70                  75                  80

Asp Ser Thr Glu Glu Gln Gln Asp Leu Phe Leu Lys Asp Met Pro Lys
                85                  90                  95

Lys Trp Leu Phe Leu Pro Phe Glu Asp Asp Leu Arg Arg Asp Leu Gly
                100                 105                 110

Arg Gln Phe Ser Val Glu Arg Leu Pro Ala Val Val Val Leu Lys Pro
            115                 120                 125

Asp Gly Asp Val Leu Thr Arg Asp Gly Ala Asp Glu Ile Gln Arg Leu
130                 135                 140

Gly Thr Ala Cys Phe Ala Asn Trp Gln Glu Ala Ala Glu Val Leu Asp
145                 150                 155                 160

Arg Asn Phe Gln Leu Pro Glu Asp Leu Glu Asp Gln Glu Pro Arg Ser
                165                 170                 175

Leu Thr Glu Cys Leu Arg Arg His Lys Tyr Arg Val Glu Lys Ala Ala
            180                 185                 190

Arg Gly Gly Arg Asp Pro Gly Gly Gly Gly Glu Glu Gly Gly Ala
            195                 200                 205

Gly Gly Leu Phe
210
```